United States Patent [19]

Schirmann et al.

[11] Patent Number: 5,750,810
[45] Date of Patent: May 12, 1998

[54] METHOD FOR COPRODUCING DIFLUOROMETHANE AND 1,1,1,2-TETRAFLUOROETHANE

[75] Inventors: Jean-Pierre Schirmann, Paris; Serge Hub, Villeurbanne; Andre Lantz, Vernaison, all of France

[73] Assignee: Elf Atochem S.A., France

[21] Appl. No.: 875,656

[22] PCT Filed: Jan. 16, 1996

[86] PCT No.: PCT/FR96/00070

§ 371 Date: Jul. 30, 1997

§ 102(e) Date: Jul. 30, 1997

[87] PCT Pub. No.: WO96/25377

PCT Pub. Date: Aug. 22, 1996

[30] Foreign Application Priority Data

Feb. 17, 1995 [FR] France ................. 95 01859

[51] Int. Cl.⁶ ................................................. C07C 17/26
[52] U.S. Cl. ................................................. 570/171
[58] Field of Search .......................................... 570/171

[56] References Cited

FOREIGN PATENT DOCUMENTS

| 508 660 | 10/1992 | European Pat. Off. . |
| 518 506 | 12/1992 | European Pat. Off. . |
| WO 91/05752 | 5/1991 | WIPO . |
| WO 91/09000 | 6/1991 | WIPO . |
| WO 95/24369 | 9/1995 | WIPO . |

*Primary Examiner*—C. Warren Ivy
*Assistant Examiner*—Garth M. Dahlen
*Attorney, Agent, or Firm*—Bell, Boyd & Lloyd

[57] ABSTRACT

The present invention relates to the simultaneous manufacture of difluoromethane (F32) and 1,1,1,2-tetrafluoroethane (F134a) by pyrolysis of chlorodifluoromethane in the presence of hydrogen, working at a temperature above 500° C. in the absence of any catalyst or metal surface. Depending on the operating conditions chosen, this process also makes it possible predominantly to manufacture either F134a or F32.

11 Claims, No Drawings

METHOD FOR COPRODUCING DIFLUOROMETHANE AND 1,1,1,2-TETRAFLUOROETHANE

FIELD OF THE INVENTION

This application is a 371 of PCT/FR96/10070, Jan. 16, 1996.

The present invention relates to the simultaneous manufacture of difluoromethane (F32) and 1,1,1,2-tetrafluoroethane (F134a) by pyrolysis of chlorodifluoromethane in the presence of hydrogen, working at a temperature above 500° C. in the absence of any catalyst or metal surface. Depending on the operating conditions chosen, this process also makes it possible predominantly to manufacture either F134a or F32.

BACKGROUND OF THE INVENTION 1,1,1,2-tetrafluoroethane (F134a) is already manufactured industrially to replace difluorodichloromethane (F12) in domestic refrigeration and motor vehicle air conditioning in particular. Two routes are currently used commercially. They involve processes which consist:

either in fluorinating trichloroethylene in two steps

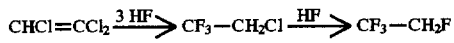

or in fluorinating perchloroethylene and then in hydrogenolysing, depending on the case, 1,1-dichloro-1,2,2,2-tetrafluoroethane (F114a) or 1-chloro-1,2,2,2-tetrafluoroethane (F124).

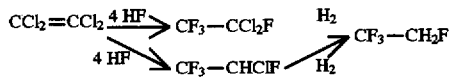

These processes require new units which are particularly expensive in investment terms and the need to use very sophisticated catalysts whose lifetime and performance are not without effect on the cost of the commercial product.

Difluoromethane $CH_2F_2$ (F32) is a potentially very advantageous compound since, in combination with pentafluoroethane (F125), it gives an azeotropic mixture which is an excellent replacement product for chlorodifluoromethane (F22) which is scheduled to be banned between 2005 and 2015 on account of its potential effect on weakening the stratospheric ozone layer.

Chlorodifluoromethane is used on a large scale as a refrigerating fluid for commercial refrigeration and for air conditioning in large buildings.

Four routes are selected for the commercial manufacture of F32:

1. Fluorination of methylene chloride $CH_2Cl_2$ with HF in the liquid phase in the presence of an antimony-based catalyst.

2. Fluorination of methylene chloride $CH_2Cl_2$ with HF in the gas phase on a chromium-based catalyst and at high temperature.

These two processes are not satisfactory since they involve the co-production of large amounts of highly toxic chlorofluoromethane (F31) (LC 50=2 ppm).

3. Hydrogenolysis of chlorodifluoromethane (F22) in the presence of a catalyst based on precious metal, at temperatures of between 200° and 300° C., or in the presence of metals such as aluminium, molybdenum, titanium, nickel, iron or cobalt at a temperature of between 300° and 700° C., as in patent application WO 91/05752.

Hydrogenolysis is entirely unselective and leads to considerable formation of methane along with smaller amounts of F31.

4. A novel process for the manufacture of F32 proposed more recently, which eliminates the co-production of F31 but is very cumbersome and relatively unselective, is based on the fluorination of formaldehyde with HF as described in patent application EP 518,506.

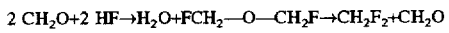

This process requires two steps and co-produces water in the presence of hydrofluoric acid, which induces high risks of corrosion.

DESCRIPTION OF THE INVENTION

Chlorodifluoromethane (F22) is currently manufactured on a large scale for commercial refrigeration but also to serve as a starting material for the production of PTFE. When the use of F22 as a refrigerant liquid is banned, it will be useful to be able to continue exploiting this compound in other applications. The present invention provides a particularly advantageous means in this respect, since it has been found that chlorodifluoromethane (F22) can be converted selectively into F134a and F32 by continuously pyrolysing F22 at a temperature of above 500° C. in the presence of hydrogen, but in the absence of metals in the reaction zone.

The amount of hydrogen used is such that the $H_2/F_{22}$ molar ratio is between 2 and 50 and more particularly between 5 and 15.

The working pressure may range up to 100 bar, but the process is generally carried out at a pressure of between 0.1 and 20 bar absolute, preferably of approximately between 0.5 and 5 bar absolute and, more particularly, at atmospheric pressure. The working temperature may be between 500° and 1000° C., but the process is preferably carried out at between 650° and 800° C.

The residence time may be between 0.1 and 100 seconds, but the process is preferably carried out for between 1 and 20 seconds. By working with short residence times, the formation of F32 is promoted, whereas with long residence times, the production of F134a is considerably increased. When the latter product is the interesting one, the F32 co-produced may obviously be recycled into the reactor in order to convert it into F134a.

Depending on the operating conditions, the F134a formed is accompanied by a variable amount of F134 ($HF_2C—CHF_2$) which is readily isomerizable into F134a.

The examples which follow illustrate the present invention in a non-limiting manner.

Examples 1 TO 6

All the examples are performed in a tubular quartz reactor 47 cm in height and 2.3 cm in diameter, placed in an electric oven with a power rating of 1.5 KW. The working pressure is atmospheric pressure and the oven temperature is measured using a thermocouple. The reactants are introduced simultaneously and continuously by means of calibrated rotameters which allow the flow rates and thus the molar ratios to be controlled. The flow of the reactants in the reactor may be diluted with a flow of inert gas such as helium or nitrogen.

All of the gas flow leaving the reactor is acidic and is conveyed to a glass reactor containing aqueous sodium hydroxide in order to remove the hydrochloric acid co-produced. The exiting gas flow is then dried over molecular sieves and then condensed at low temperature (−78° C.) in a stainless-steel container fitted with valves which allow the gaseous products to be stored at ordinary temperature.

Analysis of the gas mixtures obtained is carried out by gas chromatography coupled to mass spectrography so as to identify the reaction products with certainty.

The table below summarizes the operating conditions and the results obtained.

| EXAMPLE | Temperature (°C.) | Residence time (s) | $H_2$ mmol/h | F22 mmol/h | Conversion of F22 % | SELECTIVITY (%) TOWARDS | | | | |
|---|---|---|---|---|---|---|---|---|---|---|
| | | | | | | F32 % | $CH_4$ % | F134a % | F134 % | Balance C % |
| 1 | 550 | 14 | 473.2 | 37.4 | 32 | 41 | 0 | 36 | 19 | 98 |
| 2 | 600 | 13 | 473.2 | 37.4 | 77 | 38 | 0 | 40 | 22 | 98 |
| 3 | 650 | 12 | 473.2 | 37.4 | 97 | 39 | 0 | 40 | 18 | 97 |
| 4 | 700 | 11 | 473.2 | 37.4 | 100 | 41 | 1 | 43 | 15 | 96 |
| 5 | 650 | 12 | 473.2 | 60.3 | 98 | 32 | 1 | 40 | 23 | 99 |
| 6 | 700 | 11 | 473.2 | 60.3 | 100 | 35 | 1 | 41 | 15 | 96 |

Example 7

The process is performed as in the previous examples, in a quartz reactor 47 cm in height and 1.5 cm in diameter, with flow rates of hydrogen and of F22 of 218.8 mmol/h and 21 mmol/h respectively. Working at atmospheric pressure and with a residence time of 12.4 seconds in the isothermal region (650° C.), a 93% degree of conversion of the F22 was obtained with selectivities towards F32, F134a and F134 of 26A, 28% and 18% respectively.

Examples 8

The process was performed as above in a quartz reactor 47 cm in height and 2.1 cm in diameter, under the following conditions:

temperature: 650° C.
residence time in the 10 seconds isothermal region
pressure: 0.48 bar absolute
hydrogen flow rate: 218.8 mmol/h
F22 flow rate: 21 mmol/h The degree of conversion of the F22 was 93% with selectivities towards F32, F134a and F134 of 30%, 30% and 12% respectively.

Example 9

The process was performed in the same reactor as in Example 7, under the following conditions:

hydrogen flow rate: 513.4 mmol/h
F22 flow rate: 17.4 mmol/h
temperature: 650° C.
pressure: atmospheric
residence time in the: 2.8 seconds isothermal region The degree of conversion of the F22 was 92% with selectivities towards F32, F134a and F134 of 34%, 33% and 18% respectively.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the co-production of difluoromethane and 1,1,1,2-tetrafluoroethane, comprising pyrolysing chlorodifluoromethane in the presence of hydrogen at a temperature of above 500° C., in the absence of any catalyst or metal surface.

2. Process according to claim 1, wherein it is carried out at between 500 and 1000° C.

3. Process according to claim 1, wherein the molar ratio of hydrogen to chlorodifluoromethane is between 2 and 50.

4. Process according to claim 1, wherein the residence time is between 0.1 and 100 seconds.

5. Process according to claim 1, wherein it is carried out at a pressure of between about 0.1 and about 20 bar absolute.

6. Process according to claim 5, wherein it is carried out at a pressure of between about 0.5 and about 5 bar absolute.

7. Process according to claim 6, wherein it is carried out in a quartz reactor.

8. Process according to claim 2, wherein it is carried out between 650° and 800° C.

9. Process according to claim 3, wherein the molar ratio is between 5 and 15.

10. Process according to claim 4, wherein the residence time is between 1 and 20 seconds.

11. Process according to claim 6, wherein the pressure is atmospheric pressure.

* * * * *